US010413184B2

(12) United States Patent
Khodadad et al.

(10) Patent No.: US 10,413,184 B2
(45) Date of Patent: Sep. 17, 2019

(54) IMAGING BIOLOGICAL TISSUE OR OTHER SUBJECTS

(71) Applicant: VITAL BIOSCIENCES INC., Kitchener (CA)

(72) Inventors: Iman Khodadad, Toronto (CA); Alexander Wong, Waterloo (CA); Farnoud Kazemzadeh, Waterloo (CA)

(73) Assignee: VITAL BIOSCIENCES INC., Kitchener (CA)

( * ) Notice: Subject to any disclaimer, the term of this patent is extended or adjusted under 35 U.S.C. 154(b) by 0 days.

(21) Appl. No.: 16/136,983

(22) Filed: Sep. 20, 2018

(65) Prior Publication Data

US 2019/0082961 A1   Mar. 21, 2019

Related U.S. Application Data

(60) Provisional application No. 62/561,272, filed on Sep. 21, 2017.

(51) Int. Cl.
*A61B 5/00* (2006.01)
*A61B 8/00* (2006.01)
(Continued)

(52) U.S. Cl.
CPC ............ *A61B 5/0035* (2013.01); *A61B 5/053* (2013.01); *A61B 8/4416* (2013.01); *G16B 30/00* (2019.02)

(58) Field of Classification Search
None
See application file for complete search history.

(56) References Cited

U.S. PATENT DOCUMENTS

| 5,427,920 A | 6/1995 | Berndt et al. |
| 5,713,364 A * | 2/1998 | DeBaryshe ........ A61B 1/00059 |
| | | 250/461.2 |

(Continued)

FOREIGN PATENT DOCUMENTS

| CA | 2459110 A1 | 3/2003 |
| CA | 2750900 A1 | 8/2010 |

(Continued)

OTHER PUBLICATIONS

Sarika Singh, Health Implications of Electromagnetic Fields, Mechanisms of Action, and Research Needs, Aug. 2014, 24 pages.*

(Continued)

*Primary Examiner* — Tung S Lau
(74) *Attorney, Agent, or Firm* — Maschoff Brennan

(57) ABSTRACT

A system may include emitters configured to emit radiation at a first wavelength of electromagnetic (EM) radiation and a second wavelength of EM radiation towards a biological tissue, and receivers configured to receive responses to the first and second wavelengths of EM radiation after the wavelengths of EM radiation interact with the biological tissue. The system may also include a signal mixer unit configured to perform operations that include replicate and mix first signals representative of the responses to the first wavelength of EM radiation received by the receivers and second signals representative of the responses to the second wavelength of EM radiation received by the receivers to generate a set of spectro-spatial responses, replicate and mix the spectro-spatial responses to generate markers, and replicate and mix the markers and user-selected markers to output a sequence associated with characterization of the biological tissue.

20 Claims, 8 Drawing Sheets

(51) Int. Cl.
*A61B 5/053* (2006.01)
*G16B 30/00* (2019.01)

(56) References Cited

U.S. PATENT DOCUMENTS

| | | | | |
|---|---|---|---|---|
| 5,813,987 | A | * | 9/1998 | Modell ................ A61B 5/0062 |
| | | | | 250/216 |
| 6,058,324 | A | | 5/2000 | Chance |
| 6,103,533 | A | | 8/2000 | Hassard et al. |
| 6,118,284 | A | * | 9/2000 | Ghoshal ................ G01R 33/02 |
| | | | | 324/754.29 |
| 6,476,907 | B1 | | 11/2002 | Gordon |
| 6,870,620 | B2 | | 3/2005 | Faupel et al. |
| 2004/0147034 | A1 | * | 7/2004 | Gore ................ A61B 5/14514 |
| | | | | 436/95 |
| 2007/0127019 | A1 | * | 6/2007 | Zribi ........................ G01J 3/02 |
| | | | | 356/301 |
| 2010/0106025 | A1 | * | 4/2010 | Sarfaty ................ A61B 5/0075 |
| | | | | 600/476 |
| 2010/0267030 | A1 | * | 10/2010 | Smilansky ......... G01N 33/5005 |
| | | | | 435/6.13 |
| 2011/0059016 | A1 | * | 3/2011 | Ramanujam ......... A61B 5/0059 |
| | | | | 424/9.1 |

FOREIGN PATENT DOCUMENTS

| | | |
|---|---|---|
| CA | 2896197 A1 | 8/2014 |
| CA | 3002955 A1 | 4/2017 |

OTHER PUBLICATIONS

International Search Report dated Jan. 14, 2019 as in Application No. PCT/IB2018/057269.
Written Opinion of the International Searching Authority dated Jan. 14, 2019 as in Application No. PCT/IB2018/057269.

* cited by examiner

IMAGING BIOLOGICAL TISSUE OR OTHER SUBJECTS

FIELD

The present disclosure relates in general to the field of imaging biological tissue or other subjects, for example, by sequencing and/or characterization of biological tissue by any of a variety of methods which may include characterization of the physical state of a person based on biological tissue using electromagnetic (EM) frequency bands.

BACKGROUND

The human eye is capable of observing the visible wavelength ranges of the EM spectrum, which is a very small portion of the entire EM spectrum. If a broadband, "white" light source, such as the Sun, illuminates an object, that object would remit other wavelengths in addition to the visible wavelengths. Measuring certain characteristics of the remitted spectrum by an object can provide clues about the object's intrinsic properties. For example, these properties can include the physical state or the molecular composition of the object observed, along with other derived properties.

The subject matter claimed in the present disclosure is not limited to embodiments that solve any disadvantages or that operate only in environments such as those described above. Rather, this background is only provided to illustrate one example technology area where some embodiments described in the present disclosure may be practiced.

SUMMARY

One or more embodiments may include a method that includes emitting a first wavelength of electromagnetic (EM) radiation towards a biological tissue, and receiving, at a multiple receivers arranged in a spatial pattern, responses to the first wavelength of EM radiation after the first wavelength of EM radiation interacts with the biological tissue. The method may also include emitting a second wavelength of EM radiation towards the biological tissue, and receiving, at the receivers, responses to the second wavelength of EM radiation after the second wavelength of EM radiation interacts with the biological tissue. The method may also include performing processing on first signals that are representative of the received responses to the first wavelength of EM radiation and second signals that are representative of the received responses to the second wavelength of EM radiation. The processing may include replicating and mixing the first signals and the second signals to generate a set of spectro-spatial responses, replicating and mixing the spectro-spatial responses to generate multiple markers, and replicating and mixing the markers and user-selected markers to output a sequence associated with characterization of the biological tissue.

One or more embodiments may include a system that includes emitters configured to emit radiation at a first wavelength of electromagnetic (EM) radiation and a second wavelength of EM radiation towards a biological tissue, and receivers arranged in a spatial pattern and configured to receive responses to the first wavelength of EM radiation after the first wavelength of EM radiation interacts with the biological tissue and responses to the second wavelength of EM radiation after the second wavelength of EM radiation interacts with the biological tissue. The system may also include a signal mixer unit configured to perform operations that include replicate and mix first signals representative of the responses to the first wavelength of EM radiation received by the receivers and second signals representative of the responses to the second wavelength of EM radiation received by the receivers to generate a set of spectro-spatial responses, replicate and mix the spectro-spatial responses to generate markers, and replicate and mix the markers and user-selected markers to output a sequence associated with characterization of the biological tissue.

One or more embodiments may include a non-transitory computer-readable medium containing instructions that, when executed by a processor, are configured to cause a system to perform one or more operations. The operations may include instruct a first set of emitters to emit a first wavelength of electromagnetic (EM) radiation towards a biological tissue, and receive, from multiple receivers arranged in a spatial pattern, first signals representative of responses to the first wavelength of EM radiation after the first wavelength of EM radiation interacts with biological tissue. The operations may also include instruct a second set of emitters to emit a second wavelength of EM radiation towards the biological tissue, and receive, from the receivers, second signals representative of responses to the second wavelength of EM radiation after the second wavelength of EM radiation interacts with the biological tissue. The operations may also include perform processing on the first and the second signals, where the processing includes replicate and mix the first signals and the second signals to generate a set of spectro-spatial responses, replicate and mix the spectro-spatial responses to generate markers, and replicate and mix the markers and user-selected markers to output a sequence associated with characterization of the biological tissue.

The object and advantages of the embodiments will be realized and achieved at least by the elements, features, and combinations particularly pointed out in the claims.

It is to be understood that both the foregoing general description and the following detailed description are merely examples and explanatory and are not restrictive of the invention, as claimed.

BRIEF DESCRIPTION OF THE DRAWINGS

Example embodiments will be described and explained with additional specificity and detail through the use of the accompanying drawings in which.

DESCRIPTION OF EMBODIMENTS

Figure 1:
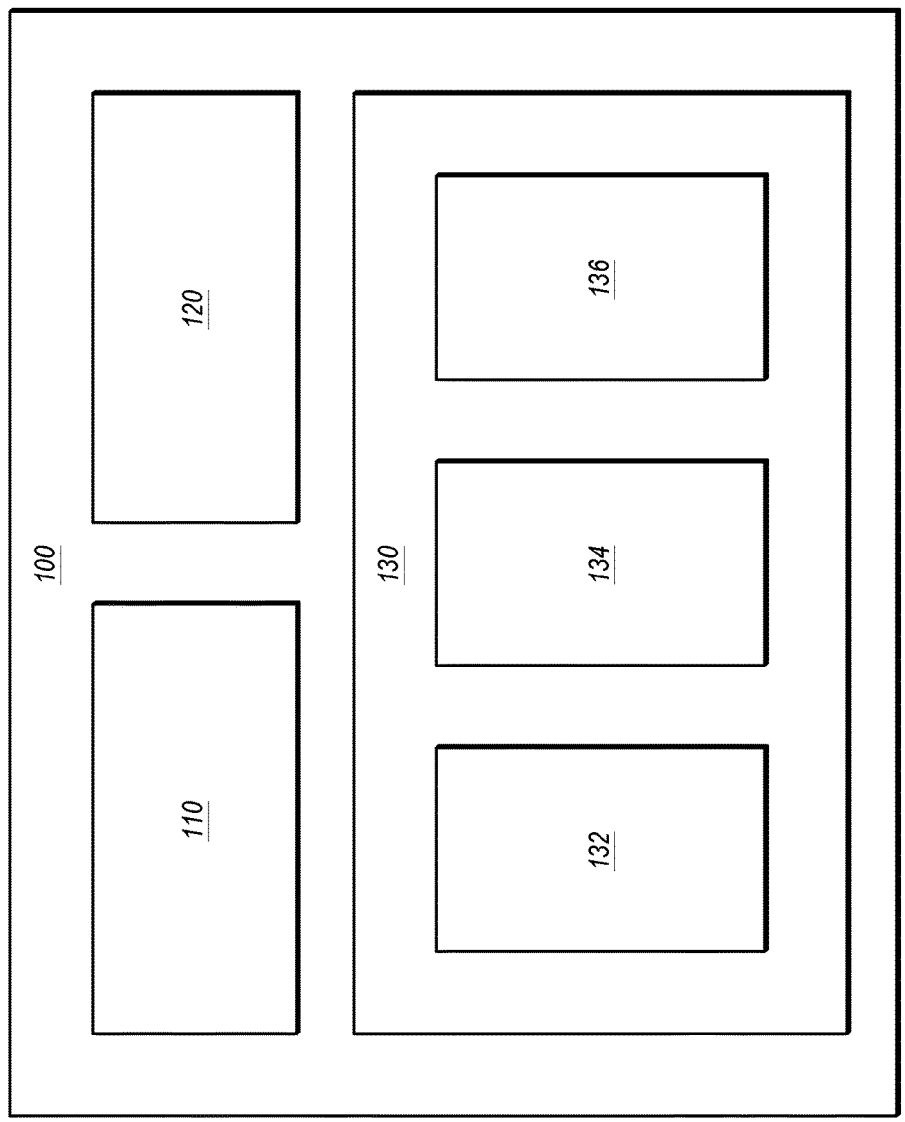
FIG. 1 illustrates an example system for imaging and/or analyzing biological tissue or other subjects.

In order to properly stage the state of a biological matter, certain fingerprints, which can reliably and robustly represent that state, need to be identified and monitored. In many cases, due to natural variances inherent in biological matters, these identifiers are smeared with noises within the received signal and one cannot deduce direct correlations with state of the biological tissue.

There are several approaches, such as multispectral (MS) or hyperspectral imaging, which are used for multi-band pass sensing. In case of imaging, one approach is to dissociate a color image, captured using a polychromatic camera, into its red, green, and blue (RGB) channels. This approach sub-divides the visible spectrum into three independent spectral bands. In such an approach, the spectral bands are highly dependent on the spectral response of the polychromatic sensor used for imaging and will vary between different sensors by different manufacturers. This approach is not a very accurate radiometric representation of targets within field-of-view (FOV) because polychromatic sensors typically use a Bayer filter to acquire the three channel RGB information and interpolate the missing spectral information in a given sensor pixel using its neighboring pixels, which do not necessarily contain similar spectral information.

One alternative approach to multi-spectral imaging employs a series of spectral bandpass filters combined with a monochromatic camera. These filters are designed to accurately transmit a wavelength range of interest while suppressing all other wavelengths. The filters can be placed in the path of the light entering the camera using approaches like a motorized filter wheel, liquid-crystal tunable filters, or acousto-optical tunable filters. Another alternative approach uses a series of light sources that can illuminate the target with light of a specific wavelength range. In this alternative approach, the remitted light is acquired on a monochromatic camera.

Some approaches perform simultaneous imaging for multi-spectral imaging using various beam splitter arrangements such that each spectral region may be imaged on its own respective camera system. Some approaches use a handheld MS imager that is limited to performing imaging in very limited spectral bands, such as the visible and the near-Infrared (NIR) spectral range. However, these systems only operate in the visible or in the NIR spectral range and are typically bulky and large. Other MS based imaging approaches are limited to the discrete EM spectrum of either the light sources or the sensor filters and therefore limited in the number of data points that can be accessed, processed, and extracted.

While previous approaches have attempted to utilize statistical models to provide a predictive analysis and diagnosis of the state of a biological matter from the photographic images or data, they have not been effective. Due to variations and large corpus of states potentially present, such previous approaches fail to determine the states accurately or with high probability.

A system and a method that can perform measurements of the signals remitted from a biological tissue, as well as, produce direct correlations that is robust to such natural variations in the state of biological tissue is disclosed. This system has the appropriate sources to radiate at various select EM bands in a controlled manner and is capable of detecting responding EM radiation (e.g., the radiation after interacting with the biological tissue) with high sensitivity.

Embodiments of the present disclosure improve upon such previous approaches. Such embodiments are explained with reference to the accompanying drawings.

FIG. 1 illustrates an example system 100 related to imaging biological tissue or other subjects, in accordance with one or more embodiments of the present disclosure. The system 100 may include one or more emitters 110, one or more receivers 120, and a signal mixer unit 130. The emitters 110 may emit EM radiation towards a subject to be imaged, and the receivers 120 may receive the EM radiation after the EM radiation has interacted with the subject. The signal mixer unit 130 may perform processing on the signals generated by the receivers 120 based on the EM radiation interactions. The signal mixer unit 130 may include a first portion 132, a second portion 134, and a third portion 136.

Figure 2:
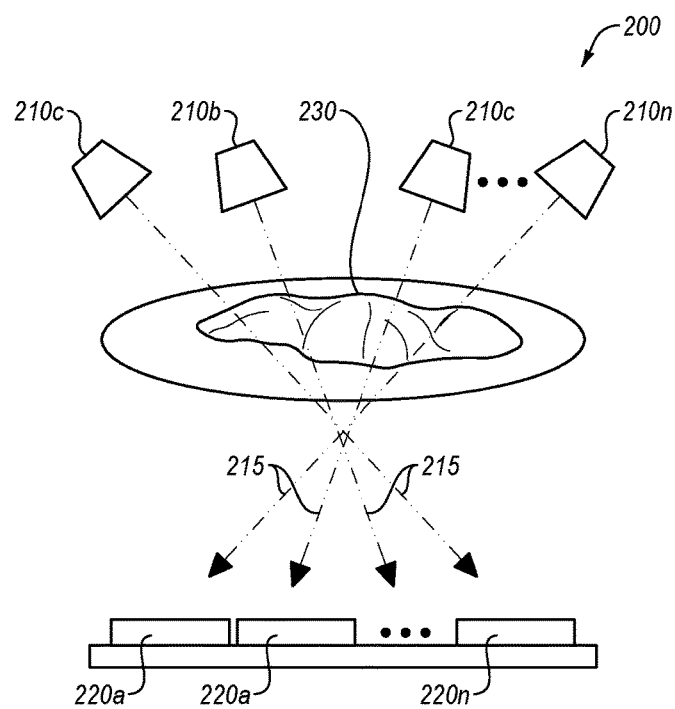
FIG. 2 illustrates an example system for imaging and/or analyzing biological tissue or other subjects using trans-illumination.
Figure 3:
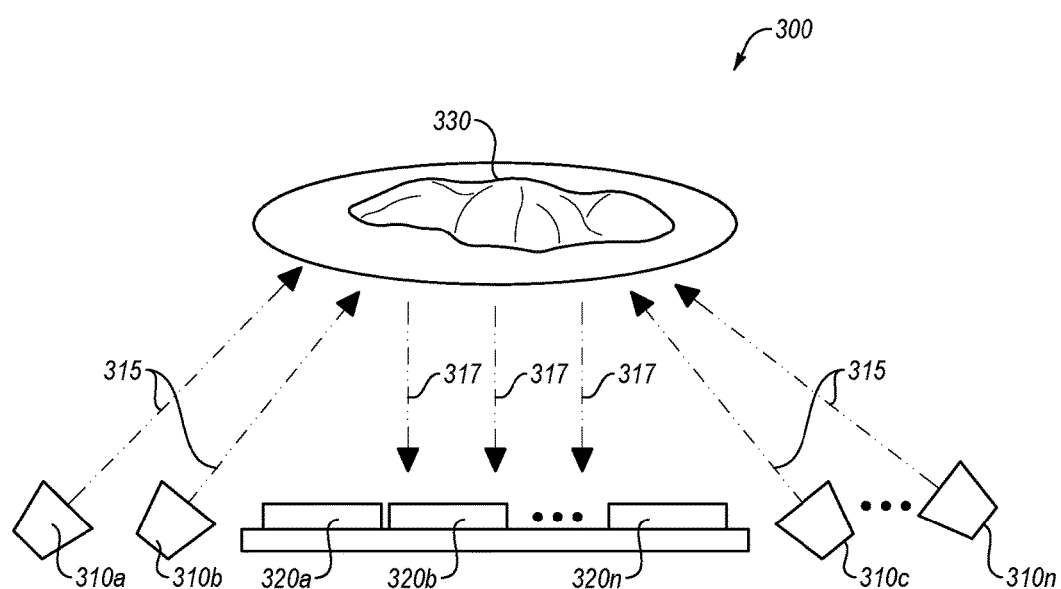
FIG. 3 illustrates an example system for imaging and/or analyzing biological tissue or other subjects using reflection.

The system 100 may be configured to perform measurements of the signals remitted from a biological tissue, as well as, produce direct correlations that are robust to such natural variations in the state of biological tissue. The system 100 may include the appropriate sources to radiate at various select EM bands in a controlled manner and is capable of detecting such emitted radiations with high sensitivity. In some embodiments the imaging of the biological tissue may be performed with trans-illumination for sublayer probing of the subject, an example of which is illustrated in FIG. 2. In some embodiments the imaging of the biological tissue may be performed with specular reflectance, an example of which is illustrated in FIG. 3.

The emitters 110 may include any system, device, or component configured to emit EM radiation. The EM radiation may include any range of EM radiation, such as radio waves, microwaves, infrared (IR) waves, visible light, ultraviolet (UV) light, x-rays, gamma rays, terahertz waves, etc. In some embodiments, the emitters 110 may include multiple emitters, where different emitters 110 are configured to emit radiation at different wavelengths, and may be independently excited to emit the radiation. Additionally or alternatively, the emitters 110 may be tunable or otherwise adjustable such that a single emitter 110 may be configured to emit multiple different wavelengths at different times (or at the same time).

In some embodiments the emitters 110 may include time interleaved independent band limited sources of EM radiation, and/or an extended bandpass source. For example, if three emitters are utilized with three distinct bands of EM radiation, the emitters may be sequentially powered to emit their respective bands of EM radiation and the target response to be detected by the receivers 120. In these and other embodiments, the combination of the emitters 110 may provide the expected excitation EM radiation interacting with the subject. The expected EM radiation may be represented by:

$$S(f) = S_0(f_0) + S_1(f_1) + \ldots + S_k(f_k)$$

where each emitted field $S_i(f_j)$ may represent the EM field emanating from the $i^{th}$ emitting source at frequency j having a specific bandpass domain. In some embodiments, the emitters 110 may provide any form of spatial radiation such as tophat, Bessel, Gaussian, etc.

The receivers 120 may include any system, device, or component configured to detect EM radiation and generate a signal representative of the EM radiation detected. In some embodiments, the receivers 120 may include multiple receivers 120 where each receiver is configured to receiver different wavelengths of EM radiation (e.g., narrow band receivers). Additionally or alternatively, a single receiver may be configured to detect radiation at multiple wavelengths (e.g., wide band receivers). In some embodiments, one or more of the receivers 120 may utilize a filter or other mechanism such that the signal detected by the receivers 120 is representative of a specific band of wavelengths, rather than all wavelengths of EM radiation received by the receiver. Such filters may be tunable or may be static filters.

In some embodiments, the EM radiation detected by the receivers 120 may be represented by:

$$D(f)=D_0(f_0)+D_1(f_1)+\ldots+D_l(f_l)$$

where the target location $D_i(f_j)$ may represent the EM field detected by the $i^{th}$ receiver at frequency j.

In some embodiments, the receivers 120 may include an imaging sensor with charged coupled devices (CCD) or complementary metal oxide semiconductor (CMOS) pixels. In one embodiment, the receivers 120 may utilize discrete filters to provide band passes over the detecting radiation. The combination and placement of such filters on the receivers 120 in addition to the time interleaved sources may provide the basis to the signal mixer unit to produce non-sparse interaction response (e.g., the signal used for estimation of status of the target). In some embodiments, the receivers 120 may include any form of an antenna that receives the EM signals in specific locations and angles.

The signal mixer unit 130 may include any system, device, or component configured to perform processing on the signals detected by the receivers 120. In some embodiments, the signal mixer unit 130 may include a computing device (such as the computing device illustrated in FIG. 9). The signal mixer unit 130 may include a first portion 132 or layer, a second portion 134 or layer, and/or a third portion 136 or layer.

In some embodiments, the signal mixer unit 130 may be implemented as an integrated circuit, as a look up table function, or as various adaptive mixing circuitries such as digital signal processing units, field programmable arrays, optical holographic units, etc. The implementation of the signal mixer unit 130 may take various forms and is not limited to a certain architecture or hardware.

The first portion 132 may be configured to replicate and mix the signals of the receivers 120 to generate a spatio-spectral response as detected by the receivers 120 that may be time-interleaved. For example, the spatio-spectral response may include values representative of the response of the subject to the EM radiation emitted by the emitters 110 and as detected by the receivers 120 across multiple spectral bands of EM radiation and across the spatial regions of the arrangement of the receivers 120.

In some embodiments, the first portion 132 may also utilize data or signals related to the receivers 120. For example, the first portion 132 may include a layer of replicator units followed by a layer of mixer units (which may be repeated in a cascade any number of times). In these and other embodiments, the time interleaved emitter 110 signals and the spatially and spectrally interleaved responses detected by the receivers 120 may be replicated and mixed to produce spatio-spectral responses from each or a combination of the individual receivers 120. Stated another way, the first portion 132 may be configured to use a combination of signals from time-multiplexed emitters 110 and signals from the spatio-spectral receivers 120 to produce a spatio-spectral matrix response from the biological tissue or other subject. In some embodiments, operations of the first portion 132 may be represented by the $k^{th}$ emitter signal of the $n^{th}$ (l=1, ..., N) mixed receiver $y(n)=[y_1(n), \ldots, y_K(n)]^T$ which is a transformation of the corresponding amplitude vector $a(n)$ of the emitter as $a(n)=[a_1(n), \ldots, a_M(n)]^T$ according to $$y(n)=g[a(n)]+e(n),$$

for n=1, ..., N, where the function g: $R^M \rightarrow R^K$ (e.g., identifying what occurs to the signal of the emitter 130 based on the EM radiation interacting with the biological tissue or sample and as detected by the receivers 120) includes a linear or nonlinear unmixer unit and $e(n)$ includes a noise sequence in the ensemble of the signals.

The second portion 134 may be configured to replicate and mix the spatio-spectral response to generate markers associated with the subject. For example, by mixing the spatio-spectral response, a set of markers may be generated that are representative of various features of the subject.

In some embodiments, a replicator unit may utilize an input signal and replicate it a multitude of times to produce output signals to feed into a set of mixer units. A mixer unit may utilize a set of input signals and perform mixing based on a mixing function to produce an output signal. In these and other embodiments, a mixing function (f) used by a signal mixer unit of the second portion 134 may be represented by $$f(x_1, x_2, \ldots, x_p) = a_1 x_1^{b_1} + a_2 x_2^{b_2} + \ldots + a_p x_p^{b_p}$$

where $a_i$ and $b_i$ are parameters corresponding to the $i^{th}$ input signal, and $x_1, x_2, \ldots, x_p$ may represent the $i^{th}$ input signal providing the spatial maps of the target (e.g., the replications for a given element of the spectro-spatial response generated by the first portion 132).

In some embodiments, the parameters of the signal mixer unit 130 may be tuned based on the desired application. For example, if imaging skin and analyzing for skin disease, the markers may include any of physiological markers, concentrations of deoxygenated hemoglobin, oxygenated hemoglobin, etc. and the parameters may be tuned accordingly. In some embodiments, the parameters may be tuned based on the received signals after any combination of linear and non-linear light-matter interactions including absorption, transmission, reflection, scattering, Raman scattering, Brillouin scattering, Rayleigh scattering, etc. In some embodiments, a map of the various markers may be generated based on the physical locations of the various markers throughout the subject, and spatial variance observed in the received signals after being unmixed by the first portion 132. For example, the concentrations of various markers at discreet spatial locations of the biological tissue or other subject may be used to produce heterogeneity maps of these markers through biological tissue or other subject. In these and other embodiments, the parameters of the signal mixer units may be tuned to enable the select physiological markers used to produce the heterogeneity maps of the target.

The third portion 136 may be configured to replicate and mix the markers of the subject and user-selected markers to generate a sequence representative of the subject. The user-selected markers may include tissue disease, shape, size, etc. The sequence may operate as a fingerprint or barcode via which the state of the subject may be determined. For example, various portions of the sequence may be identified and/or compared to other reference portions of the sequence to identify the state of the subject. The sequence may be referred to as a radiomic sequence and may include any number of parameters, such as thousands of parameters. The sequence may provide a highly specific (or even unique) fingerprint for the states of a biological matter and may act as a key to such states, analogous to a genomic sequence. For example, just as various portions of a genomic sequence may be identified as corresponding to a given protein to be coded, a sequence or portion of the radiomic sequence may identify a particular state of the biological tissue or other subject.

In some embodiments, the operation of the third portion 136 may be represented by the mixing function $$s(w_1, w_2, \ldots, w_u) = c_1 r_1^{d_1} + c_2 r_2^{d_2} + \cdots + c_u r_u^{d_u}$$

where $c_u$ and $d_u$ are parameters corresponding to the $u^{th}$ marker or user-selected marker ($r_u$), and s( . . . ) represents the sequence that is output by the third portion 136.

In some embodiments, the system 100 may output the sequence generated by the third portion 136 and provide it to a comparative agent or machine. The comparative agent or machine may compare the sequence with a bank of known pre-verified sequences to predict a given state of the biological tissue or other subject, and/or an associated prognosis.

Modifications, additions, or omissions may be made to FIG. 1 without departing from the scope of the present disclosure. For example, the system 100 may include more components or fewer components than those illustrated.

FIG. 2 illustrates an example system 200 for imaging and/or analyzing biological tissue 230 or other subjects using trans-illumination, in accordance with one or more embodiments of the present disclosure. As illustrated in FIG. 2, one or more emitters 210 (e.g., the emitters 210a, 210b, . . . , 210n) may be configured to emit EM radiation 215 that is received by one or more receivers 220 (e.g., the receivers 220a, 220b, . . . , 220c) after interacting with biological tissue 230 (or some other subject).

As illustrated in FIG. 2, the emitters 210 may be positioned and arranged such that the EM radiation may pass through the biological tissue 230 before the response thereof is received by the receivers 220. As the EM radiation 215 passes through the biological tissue 230, the response thereto may be modified, reflected, refracted, scattered, etc. by interacting with the biological tissue 230. In these and other embodiments and as described herein, utilizing the EM radiation 215 as output by the emitters 210 and the EM radiation 215 as detected by the receivers 220, a sequence associated with the biological tissue 230 may be generated.

In some embodiments, the interaction with the tissue may include any combination of linear or non-linear light-matter interactions. For example, the interactions may include any of absorption, transmission, reflection, scattering, Raman scattering, Brillouin scattering, ad Rayleigh scattering, etc.

Modifications, additions, or omissions may be made to FIG. 2 without departing from the scope of the present disclosure.

FIG. 3 illustrates an example system 300 for imaging and/or analyzing biological tissue 300 or other subjects using reflection, in accordance with one or more embodiments of the present disclosure. As illustrated in FIG. 3, one or more emitters 310 (e.g., the emitters 310a, 310b, . . . , 310n) may be configured to emit EM radiation 315 that interacts with and is reflected back by the biological tissue 330 as a reflected EM response 317 and received by one or more receivers 320.

As illustrated in FIG. 3, the emitters 310 may be positioned and arranged such that the EM radiation 315 may be reflected back generally in a similar direction to a location of the emitters 310 off of the biological tissue 330 before being received by the receivers 320. As the EM radiation 315 is reflected by the biological tissue 330, the reflected EM radiation 317 may be modified as compared to the initial EM radiation 315 based on the properties of the biological tissue 330. In these and other embodiments and as described herein, utilizing the EM radiation 315 as output by the emitters 310 and the EM radiation 317 as detected by the receivers 320, a spatio-spectral response associated with the biological tissue 330 may be generated.

Modifications, additions, or omissions may be made to FIG. 3 without departing from the scope of the present disclosure.

Figure 4:
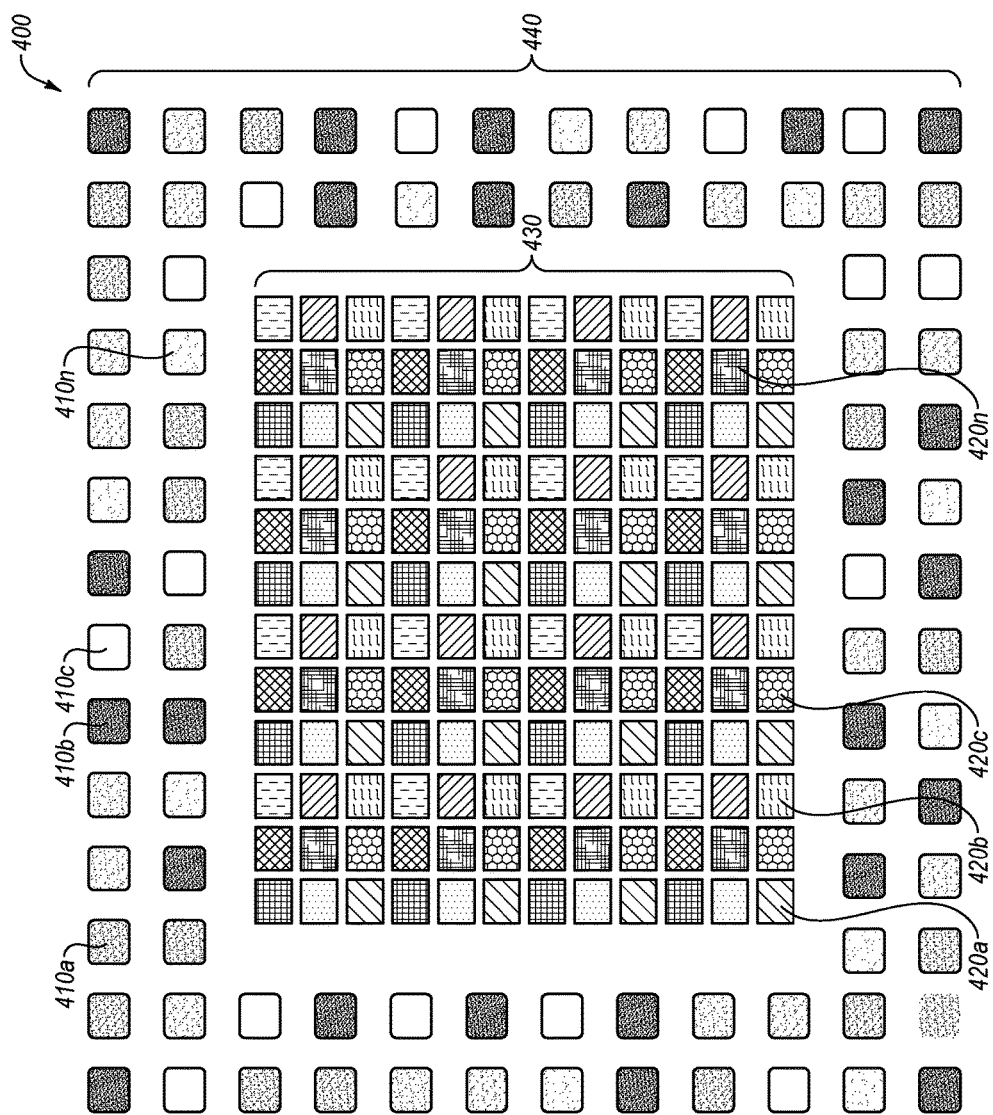
FIG. 4 illustrates an example one arrangement of emitters and receivers to facilitate imaging and/or analyzing of a biological tissue or other subjects.

FIG. 4 illustrates an example system 400 of one arrangement of emitters 410 and receivers 420 to facilitate imaging and/or analyzing of a biological tissue or other subjects, in accordance with one or more embodiments of the present disclosure.

As illustrated in FIG. 4, in some embodiments, the emitters 410 may include a first emitter 410a configured to emit radiation at a first wavelength, a second emitter 410b configured to emit radiation at a second wavelength, etc. In these and other embodiments, the receivers 420 may include a first receiver 420a configured to detect EM responses at a first band of wavelengths, a second receiver 420b configured to detect radiation at a second band of wavelengths, etc. The various hashmarks illustrate that the various emitters 410 and/or receivers 420 may be configured to operate at a particular spectral, temporal, and/or polarized sequence, or some portion or any combination of any of the foregoing.

In some embodiments, the receivers 420 may be positioned in a central region 430 that may correspond generally with a biological tissue or other subject. For example, the biological tissue may be positioned relative to the receivers 420 such that as EM response is reflected off of the biological tissue it is directed towards the receivers 420.

In some embodiments, the emitters 410 may be positioned in an outer region 440 that goes around the central region 430.

While one embodiment is illustrated in FIG. 4, it will be appreciated that any arrangement of emitters 410 and receivers 420 are contemplated within the present disclosure. For example, the emitters 410 and the receivers 420 may be interspersed among each other. As another example, the emitters 410 may be in the central region 430 and the receivers 420 may be in the outer region 440.

Modifications, additions, or omissions may be made to the system 400 without departing from the scope of the present disclosure. For example, any number of arrangements of emitters 410 and receivers 420 are contemplated.

Figure 5:
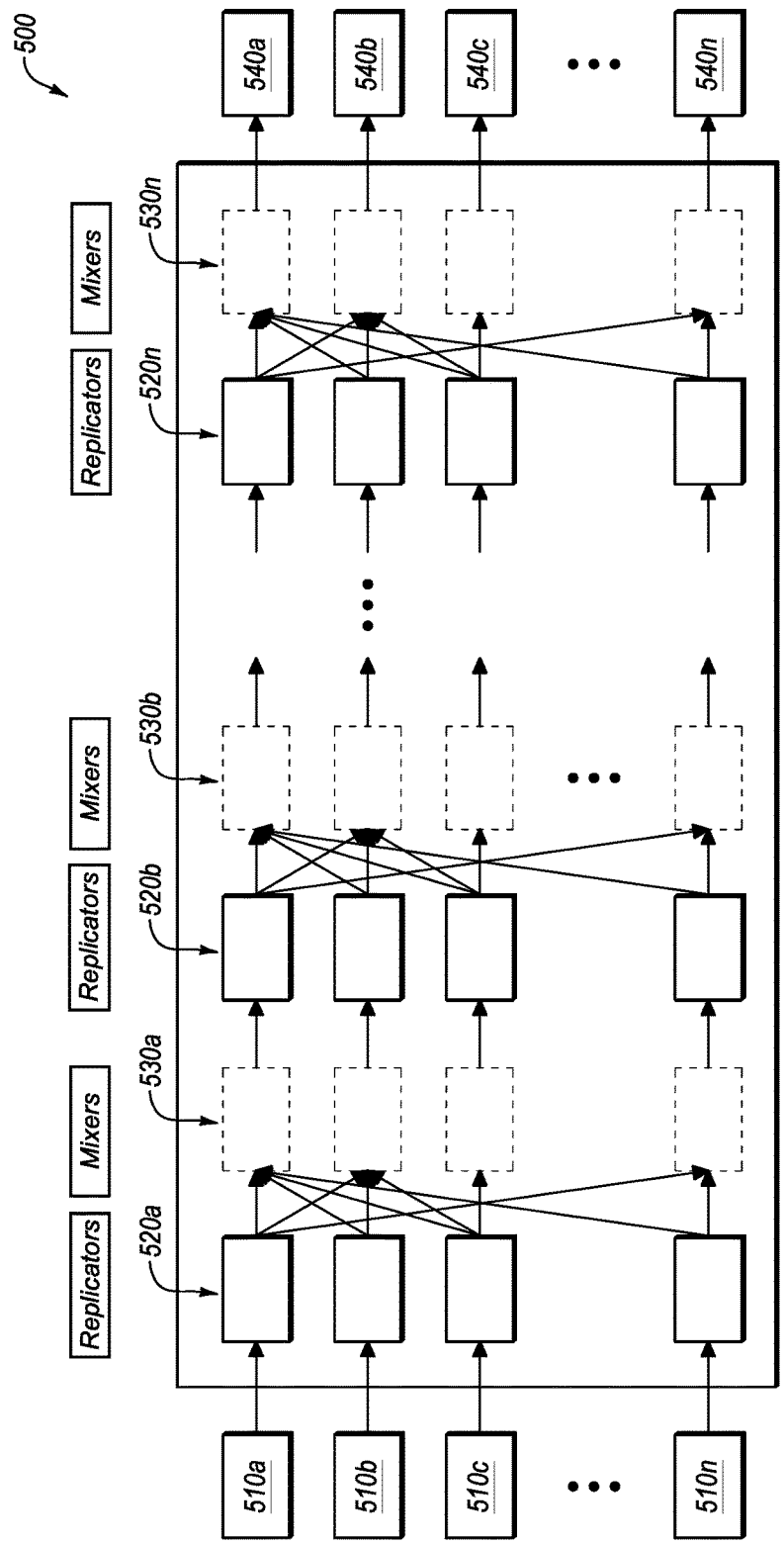
FIG. 5 illustrates an example of a first portion of a signal mixer device.

FIG. 5 illustrates an example of a first portion 500 of a signal mixer device, in accordance with one or more embodiments of the present disclosure. As illustrated in FIG. 5, the first portion 500 may receive as input one or more of the received signals 510 (e.g., received signals 510a, 510b, . . . , 510n) as detected by the receivers and/or as emitted by the emitters and interacting with the target. The first portion 500 includes a first set of replicators 520a that replicate the input signals a number of times and pass those signals to one or more mixer unites 530a. The output of the mixer units 530a may be used as the input signal for the next cascade of replicators 520b. The output of the replicators 530b may be used as the inputs for the mixer units 530b. While three iterations of the cascade of replicators 520 and mixers 530 are illustrated, any number of iterations of replicators 520 and mixers 530 (e.g., up to the replicators 520n and mixers 530n) are contemplated within the present disclosure.

After the cascade of replicators 520 and mixers 530, the first portion 500 may output a series of spectro-spatial responses 540a-n. In some embodiments, the number of spectro-spatial responses 540 may be based on the number of frequency bands emitted, the number of frequency bands selected for by the receivers, the number of distinct spatial signals received, the number of receivers, the number of emitters, the combination set of emitters emitting at a subset of bands at the same time, etc.

Modifications, additions, or omissions may be made to the first portion 500 without departing from the scope of the present disclosure. For example, any number of iterations of the cascade of replicators 520 and mixers 530 may be included.

Figure 6:
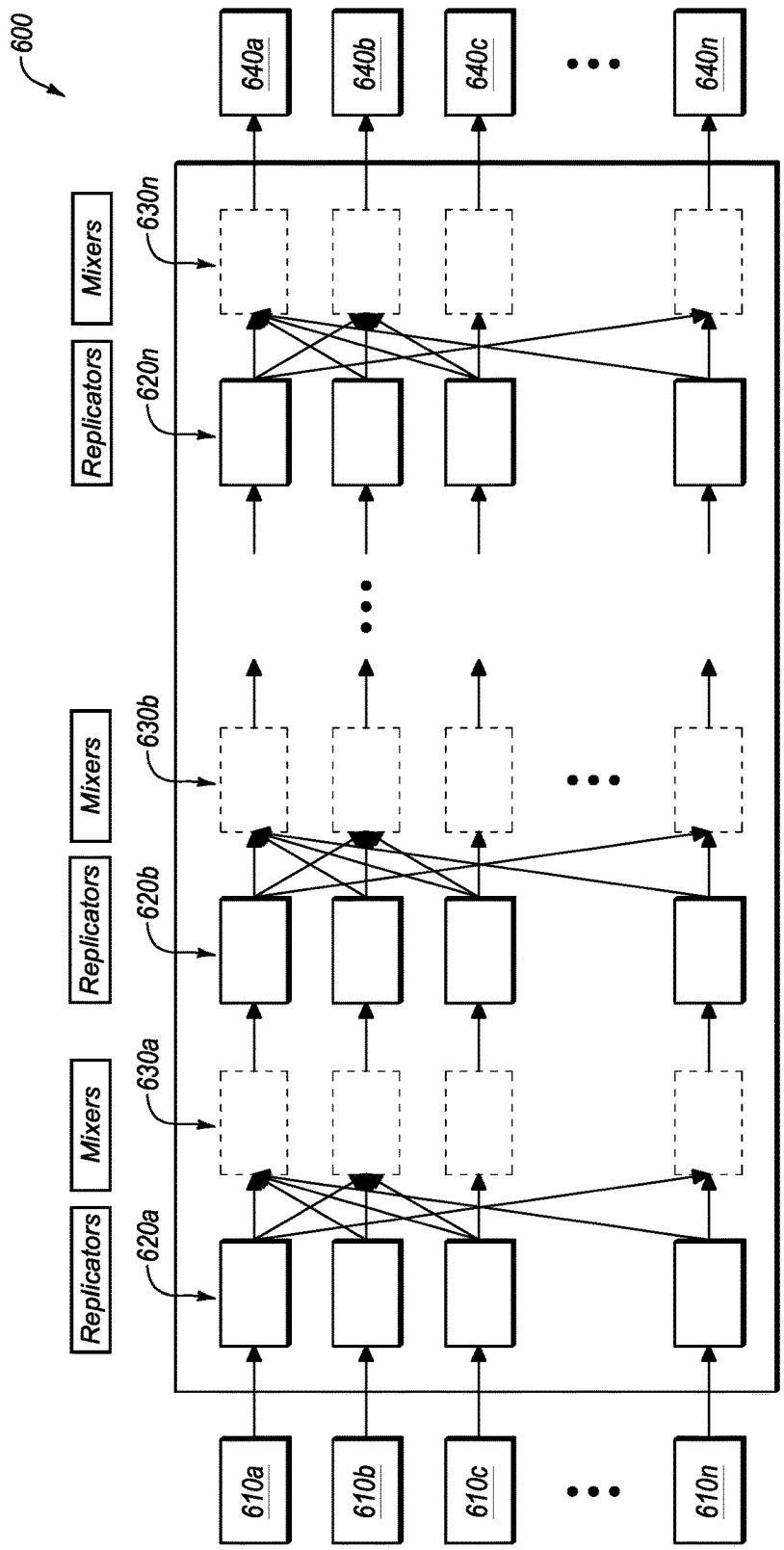
FIG. 6 illustrates an example of a second portion of a signal mixer device.

FIG. 6 illustrates an example of a second portion of a signal mixer device 600, in accordance with one or more embodiments of the present disclosure. As illustrated in FIG. 6, the second portion 600 may receive as input the spatio-spectral responses 610 (e.g., the spatio-spectral responses 610 as output by the first portion 500 of FIG. 5). The second portion 600 includes a first set of replicators 620a that replicate the input signals a number of times and pass those signals to one or more mixer unites 630a. The output of the mixer units 630a may be used as the input signal for the next cascade of replicators 620b. The output of the replicators 630b may be used as the inputs for the mixer units 630b. While three iterations of the cascade of replicators 620 and mixers 630 are illustrated, any number of iterations of replicators 620 and mixers 630 (e.g., up to the replicators 620n and mixers 630n) are contemplated within the present disclosure.

After the cascade of replicators 620 and mixers 630, the second portion 600 may output a set of markers 640a-n.

Modifications, additions, or omissions may be made to the second portion 600 without departing from the scope of the present disclosure. For example, any number of iterations of the cascade of replicators 620 and mixers 630 may be included.

Figure 7:
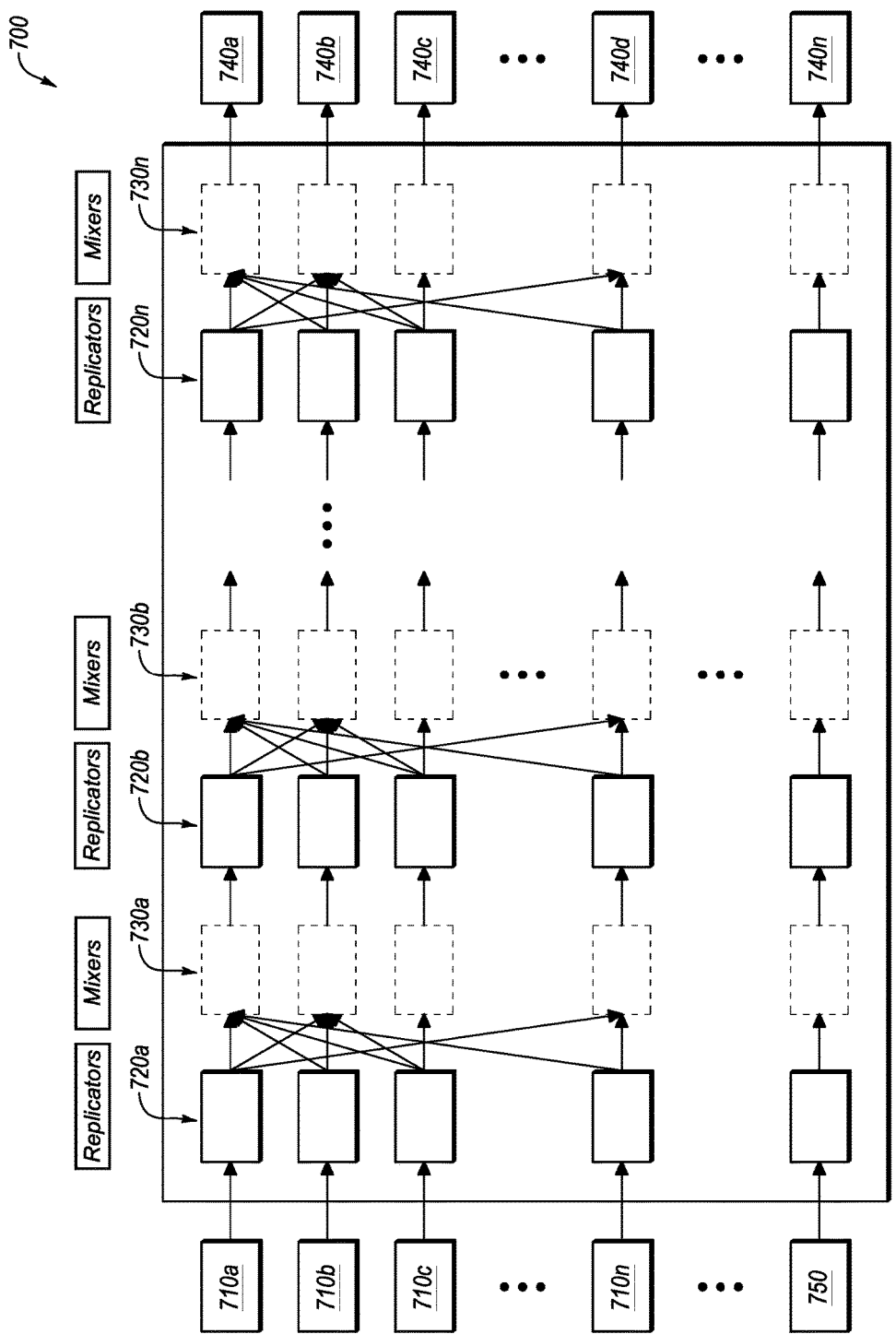
FIG. 7 illustrates an example of a third portion of a signal mixer device.

FIG. 7 illustrates an example of a third portion 700 of a signal mixer device, in accordance with one or more embodiments of the present disclosure. As illustrated in FIG. 7, the third portion 700 may receive as input the produced markers 710 (e.g., the markers 640 as output by the second portion 600 of FIG. 6). Additionally or alternatively, the third portion 700 may receive as inputs a set of user-defined markers 750. In some embodiments, the third portion 700 includes a first set of replicators 720a that replicate the input signals a number of times and pass those signals to one or more mixer unites 730a. The output of the mixer units 730a may be used as the input signal for the next cascade of replicators 720b. The output of the replicators 730b may be used as the inputs for the mixer units 730b. While three iterations of the cascade of replicators 720 and mixers 730 are illustrated, any number of iterations of replicators 720 and mixers 730 (e.g., up to the replicators 720n and mixers 730n) are contemplated within the present disclosure.

After the cascade of replicators 720 and mixers 730, the second portion 700 may output an array of values 740a-n as a sequence corresponding to the biological sample or other subject being imaged.

Modifications, additions, or omissions may be made to the third portion 700 without departing from the scope of the present disclosure. For example, any number of iterations of the cascade of replicators 720 and mixers 730 may be included.

Figure 8:
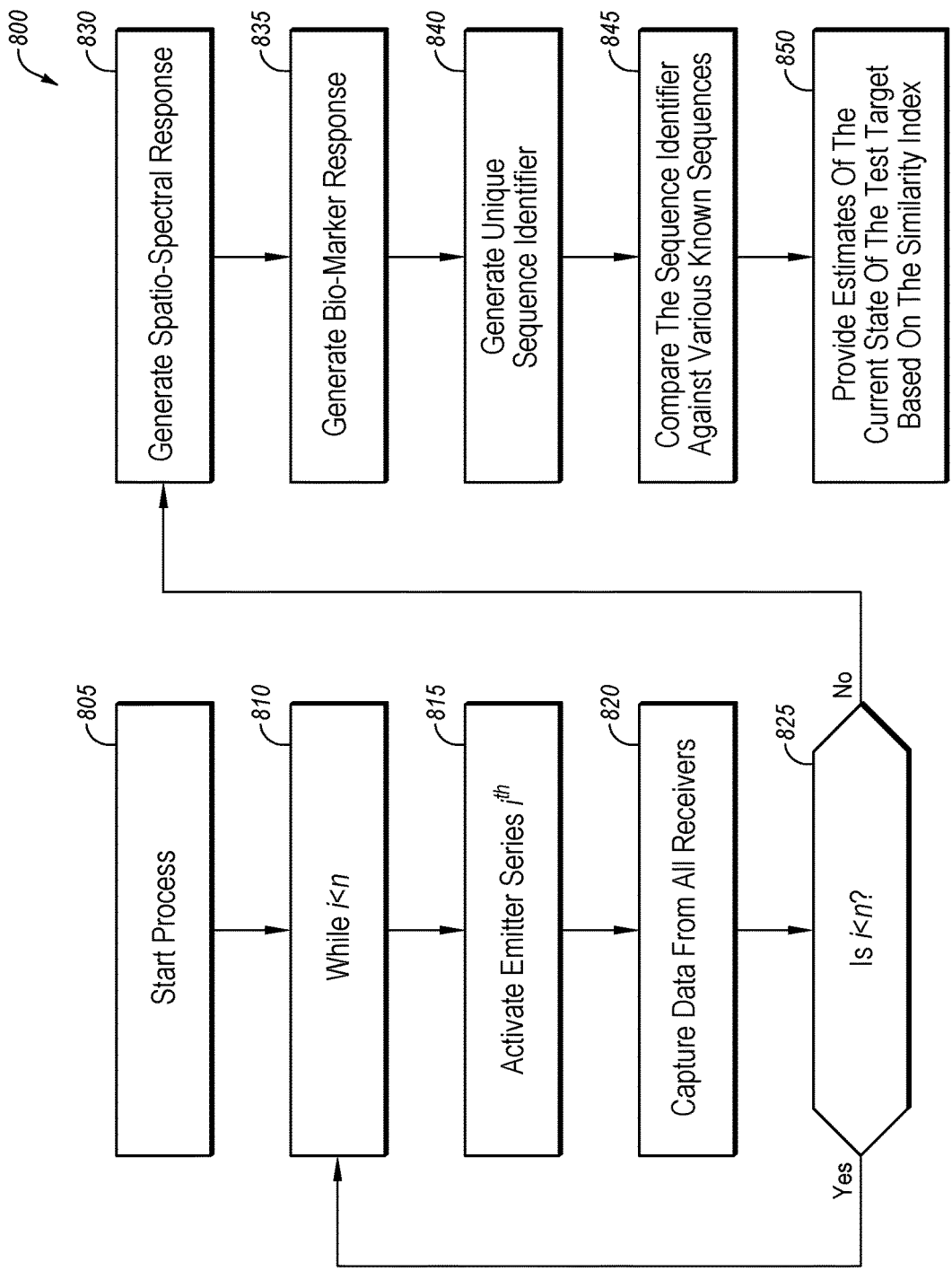
FIG. 8 illustrates an example flow diagram of an example method of imaging and/or analyzing biological tissue or other subjects.

FIG. 8 illustrates a flowchart of an example method 800 of imaging biological tissue or other subject, in accordance with one or more embodiments of the present disclosure.

At block 805 the method 800 may begin. For example, one or more counting variables may be initialized, such as the variable i.

At block 810, a determination may be made whether i<n, or stated another way, whether the method 800 has gone through to capture data for each of the distinct emitter sets. While i continues to be less than n the method 800 proceeds to the block 815.

At block 815, the $i^{th}$ emitter series may be activated. For example, a subset of all the emitters may be activated, where the subset emits at a given bandwidth of EM frequency or frequencies. As another example, one or more of the emitters may be tuned to a certain frequency and may be activated.

At block 820, data may be captured from the receivers. For example, the receivers that are configured to detect a band of EM frequencies within which the emitters are emitting at block 815 may convert the received signals into a readable signal that may be captured to be used in processing.

At block 825, a determination may be made whether i<n, or stated another way, whether the method 800 has gone through to capture data for each of the distinct emitters. If it is determined that i is less than n, the method 800 may increment i and return to the block 810 such that another series of emitters may be activated (at block 815) and the corresponding data may be captured (at block 820). If it is determined that i is not less than n (e.g., all the series of emitters have been activated), the method 800 may proceed to the block 830.

At block 830, a spatio-spectral response may be generated. For example, the operation at the block 830 may perform the operations associated with the first portion of the signal mixer unit as described in the present disclosure.

At block 835, a set of markers may be generated. For example, the operation at the block 840 may perform the operations associated with the second portion of the signal mixer unit as described in the present disclosure.

At block 840, a sequence may be generated. For example, the operation at the block 850 may perform the operations associated with the third portion of the signal mixer unit as described in the present disclosure.

At block 845, the sequence may be compared to various known sequences. For example, known sequences may correspond to various disease conditions, health conditions, physiological statuses, etc. such that the sequence of block 840 may be compared to other known sequences.

At block 850, based on the comparison of block 845, estimates may be provided regarding the current state of the biological tissue or other subject based on a similarity index with the known sequences. For example, if the sequence at issue includes a portion that is nearly identical to a known sequence corresponding to some state, a high-confidence estimate may be provided regarding the state of the biological tissue that corresponds to the known state. In these and other embodiments, the similarity between the sequence being analyzed and the known sequences may be determined numerically, statistically, or by any other mathematical comparison.

Modifications, additions, or omissions may be made to the method 800 without departing from the scope of the present disclosure. For example, the operations may be performed in a differing order. As another example, additional operations may be added to, or performed in conjunction with the operations of the method 800. As an additional example, operations may be added, omitted, and/or performed simultaneously. As another example, various operations may be combined into a single operation, or a single operation may be divided into multiple operations.

Figure 9:
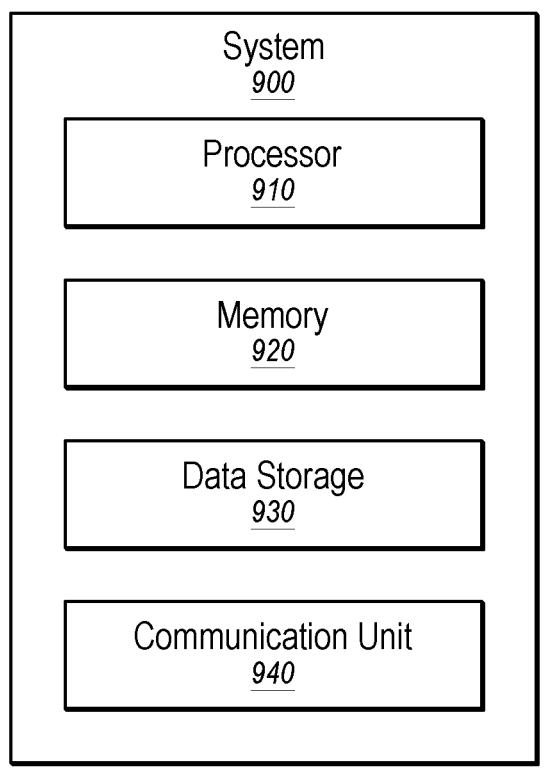
FIG. 9 illustrates an example computing system.

FIG. 9 illustrates an example computing system 900, according to at least one embodiment described in the present disclosure. The system 900 may include any suitable system, apparatus, or device configured to communicate over a network. The computing system 900 may include a processor 910, a memory 920, a data storage 930, and a communication unit 940, which all may be communicatively coupled. The data storage 930 may include various types of data, such as software projects, API documents, computer source code, etc.

Generally, the processor 910 may include any suitable special-purpose or general-purpose computer, computing entity, or processing device including various computer hardware or software modules and may be configured to execute instructions stored on any applicable computer-readable storage media. For example, the processor 910 may include a microprocessor, a microcontroller, a digital signal processor (DSP), an application-specific integrated circuit (ASIC), a Field-Programmable Gate Array (FPGA), or any other digital, analog, or optical circuitry configured to interpret and/or to execute program instructions and/or to process data.

Although illustrated as a single processor in FIG. 9, it is understood that the processor 910 may include any number of processors distributed across any number of network or physical locations that are configured to perform individually or collectively any number of operations described in the present disclosure. In some embodiments, the processor 910 may interpret and/or execute program instructions and/or process data stored in the memory 920, the data storage 930, or the memory 920 and the data storage 930. In some embodiments, the processor 910 may fetch program instructions from the data storage 930 and load the program instructions into the memory 920.

After the program instructions are loaded into the memory 920, the processor 910 may execute the program instructions, such as instructions to perform one or more operations of the method 800 of FIG. 8. For example, the processor 910 may obtain instructions regarding directing emitters to emit EM radiation at certain frequencies, receive signals from receivers representing received EM radiation after interacting with a biological tissue or other subject, and perform processing on the signals to provide, such as reproducing and mixing various aspects or features of the signals to derive a sequence from which the state of the biological tissue or sample can be determined.

The memory 920 and the data storage 930 may include computer-readable storage media or one or more computer-readable storage mediums for carrying or having computer-executable instructions or data structures stored thereon. Such computer-readable storage media may be any available media that may be accessed by a general-purpose or special-purpose computer, such as the processor 910. In some embodiments, the computing system 900 may or may not include either of the memory 920 and the data storage 930.

By way of example, and not limitation, such computer-readable storage media may include non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store desired program code in the form of computer-executable instructions or data structures and which may be accessed by a general-purpose or special-purpose computer. Combinations of the above may also be included within the scope of computer-readable storage media. Computer-executable instructions may include, for example, instructions and data configured to cause the processor 910 to perform a certain operation or group of operations.

The communication unit 940 may include any component, device, system, or combination thereof that is configured to transmit or receive information over a network. In some embodiments, the communication unit 940 may communicate with other devices at other locations, the same location, or even other components within the same system. For example, the communication unit 940 may include a modem, a network card (wireless or wired), an optical communication device, an infrared communication device, a wireless communication device (such as an antenna), and/or chipset (such as a Bluetooth device, an 802.6 device (e.g., Metropolitan Area Network (MAN)), a WiFi device, a WiMax device, cellular communication facilities, or others), and/or the like. The communication unit 940 may permit data to be exchanged with a network and/or any other devices or systems described in the present disclosure. For example, the communication unit 940 may allow the system 900 to communicate with other systems, such as computing devices and/or other networks. As another example, the communication unit 940 may communicate with emitters and/or receivers.

Modifications, additions, or omissions may be made to the system 900 without departing from the scope of the present disclosure. For example, the data storage 930 may be multiple different storage mediums located in multiple locations and accessed by the processor 910 through a network.

As indicated above, the embodiments described in the present disclosure may include the use of a special purpose or general purpose computer (e.g., the processor 910 of FIG. 9) including various computer hardware or software modules, as discussed in greater detail below. Further, as indicated above, embodiments described in the present disclosure may be implemented using computer-readable media (e.g., the memory 920 or data storage 930 of FIG. 9) for carrying or having computer-executable instructions or data structures stored thereon.

As used in the present disclosure, the terms "module" or "component" may refer to specific hardware implementations configured to perform the actions of the module or component and/or software objects or software routines that may be stored on and/or executed by general purpose hardware (e.g., computer-readable media, processing devices, or some other hardware) of the computing system. In some embodiments, the different components, modules, engines, and services described in the present disclosure may be implemented as objects or processes that execute on the computing system (e.g., as separate threads). While some of the systems and methods described in the present disclosure are generally described as being implemented in software (stored on and/or executed by general purpose hardware), specific hardware implementations or a combination of software and specific hardware implementations are also possible and contemplated. In this description, a "computing entity" may be any computing system as previously defined in the present disclosure, or any module or combination of modulates running on a computing system.

In accordance with common practice, the various features illustrated in the drawings may not be drawn to scale. The illustrations presented in the present disclosure are not meant to be actual views of any particular apparatus (e.g., device, system, etc.) or method, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method.

Terms used in the present disclosure and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," among others).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc.

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

Additionally, the use of the terms "first," "second," "third," etc., are not necessarily used herein to connote a specific order or number of elements. Generally, the terms "first," "second," "third," etc., are used to distinguish between different elements as generic identifiers. Absence a showing that the terms "first," "second," "third," etc., connote a specific order, these terms should not be understood to connote a specific order. Furthermore, absence a showing that the terms "first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

All examples and conditional language recited in the present disclosure are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

What is claimed is:

1. A method, comprising:
   emitting a first wavelength of electromagnetic (EM) radiation towards a biological tissue;
   receiving, at a plurality of receivers arranged in a spatial pattern, responses to the first wavelength of EM radiation after the first wavelength of EM radiation interacts with the biological tissue;
   emitting a second wavelength of EM radiation towards the biological tissue;
   receiving, at the plurality of receivers, responses to the second wavelength of EM radiation after the second wavelength of EM radiation interacts with the biological tissue;
   performing processing on first signals representative of the received responses to the first wavelength of EM radiation and second signals representative of the received responses to the second wavelength of EM radiation, the processing including:
      replicating and mixing the first signals and the second signals to generate a set of spectro-spatial responses;
      replicating and mixing the spectro-spatial responses to generate a plurality of markers; and
      replicating and mixing the plurality of markers and a plurality of user-selected markers to output a sequence associated with characterization of the biological tissue.

2. The method of claim 1, wherein the first wavelength of EM radiation is emitted by a first EM emitter and the second wavelength of EM radiation is emitted by a second EM emitter different from the first EM emitter.

3. The method of claim 1, wherein a first subset of the plurality of receivers each includes a first filter to exclude the second wavelength of EM radiation, and a second subset of the plurality of receivers each includes a second filter to exclude the second wavelength of EM radiation.

4. The method of claim 3, wherein receiving at the plurality of receivers includes, for at least a given receiver of the first subset of the plurality of receivers, both generating signals representative of the responses to the first wavelength of EM radiation, and using the first filter to exclude the responses to the second wavelength of EM radiation.

5. The method of claim 1, further comprising comparing the sequence with known sequences to predict a state of the biological tissue.

6. The method of claim 5, wherein the state includes a prognosis of one or more diseases related to the biological tissue.

7. The method of claim 1, wherein the plurality of receivers are positioned to receive the responses to the first wavelength of EM radiation and the responses to the second wavelength of EM radiation after reflecting off of the biological tissue.

8. The method of claim 1, wherein the plurality of receivers are positioned to receive the responses to the first wavelength of EM radiation and the responses to the second wavelength of EM radiation after transmission through the biological tissue.

9. The method of claim 1, wherein the replicating and mixing the first signals and the second signals to generate a set of spectro-spatial responses includes utilizing a nonlinear function and a mapping of the plurality of receivers to derive a spectro-spatial matrix as the set of spectro-spatial responses, where the $k^{th}$ emitter signal of the $n^{th}$ (l=1, ..., N) mixed pixel $y(n)=[y_1(n), \ldots, y_K(n)]^T$ is a transformation of its corresponding amplitude vector $a(n)=[a_1(n), \ldots, a_M(n)]^T$ according to $y(n)=g[a(n)]+e(n)$, for n=1, ..., N, where g: $R^M \rightarrow R^K$ includes a linear or nonlinear mixer unit and e(n) includes a noise sequence in the first and the second signals.

10. The method of claim 1, wherein the replicating and mixing the spectro-spatial responses to generate a plurality of markers includes:
replicating each element of the set of spectro-spatial responses a plurality of times; and
for each element of the set of spectro-spatial responses, utilizing the replicated signals as input signals for the mixing, where the mixing utilizes a mixing function $f$:

$$f(x_1, x_2, \ldots, x_p) = a_1 x_1^{b_1} + a_2 x_2^{b_2} + \ldots + a_p x_p^{b_p}$$

where $a_i$ and $b_i$ are parameters corresponding to the $i^{th}$ input signal, and $x_1, x_2, \ldots, x_p$ represent the plurality of replications for a given element of the spectro-spatial response.

11. The method of claim 10, wherein the parameters are tuned based on the biological tissue.

12. The method of claim 1, wherein the replicating and mixing the plurality of markers and the plurality of user-selected markers to output a sequence associated with the biological tissue includes:
replicating each of the plurality of markers a plurality of times; and
mixing each of the plurality of markers with the user-selected markers to yield the sequence (s) based on:

$$s(w_1, w_2, \ldots, w_u) = c_1 r_1^{d_1} + c_2 r_2^{d_2} + \ldots + c_u r_u^{d_u}$$

where $c_u$ and $d_u$ are parameters corresponding to the $u^{th}$ marker or user-selected marker ($r_u$).

13. The method of claim 1, wherein the first wavelength of EM radiation and the second wavelength of EM radiation are emitted at a same time.

14. The method of claim 1, wherein the response to the first wavelength of EM radiation is based on at least one of absorption, transmission, reflection, scattering, Raman scattering, Brillouin scattering, and Rayleigh scattering.

15. A system, comprising:
a plurality of emitters configured to emit radiation at a first wavelength of electromagnetic (EM) radiation and a second wavelength of EM radiation towards a biological tissue;
a plurality of receivers arranged in a spatial pattern and configured to receive responses to the first wavelength of EM radiation after the first wavelength of EM radiation interacts with the biological tissue and responses to the second wavelength of EM radiation after the second wavelength of EM radiation interacts with the biological tissue;
a signal mixer unit configured to perform operations, the operations including:
replicate and mix first signals representative of the responses to the first wavelength of EM radiation received by the plurality of receivers and second signals representative of the responses to the second wavelength of EM radiation received by the plurality of receivers to generate a set of spectro-spatial responses;
replicate and mix the spectro-spatial responses to generate a plurality of markers; and
replicate and mix the plurality of markers and a plurality of user-selected markers to output a sequence associated with characterization of the biological tissue.

16. The system of claim 13, wherein the signal mixer unit includes one of an analog or digital processing device implemented via an electronic, optical, or chemical subsystem.

17. The system of claim 13, wherein the plurality of emitters are arranged in an outside region surrounding where the plurality of receivers are located.

18. The system of claim 13, wherein the plurality of emitters includes a first subset of the plurality of emitters configured to emit EM radiation at the first wavelength and a second subset of the plurality of emitters configured to emit EM radiation at the second wavelength.

19. A non-transitory computer-readable medium containing instructions that, when executed by a processor, are configured to cause a system to perform one or more operations, the operations comprising:
instruct a first plurality of emitters to emit a first wavelength of electromagnetic (EM) radiation towards a biological tissue;
receive, from a plurality of receivers arranged in a spatial pattern, first signals representative of responses to the first wavelength of EM radiation after the first wavelength of EM radiation interacts with biological tissue;
instruct a second plurality of emitters to emit a second wavelength of EM radiation towards the biological tissue;
receive, from the plurality of receivers, second signals representative of responses to the second wavelength of EM radiation after the second wavelength of EM radiation interacts with the biological tissue;
perform processing on the first and the second signals, the processing including:
replicate and mix the first signals and the second signals to generate a set of spectro-spatial responses;
replicate and mix the spectro-spatial responses to generate a plurality of markers; and
replicate and mix the plurality of markers and a plurality of user-selected markers to output a sequence associated with characterization of the biological tissue.

20. The computer-readable medium of claim 19, the operations further comprising compare the sequence with known sequences to predict a state of the biological tissue.

* * * * *